US00PP13191P2

(12) United States Plant Patent
Utecht

(10) Patent No.: US PP13,191 P2
(45) Date of Patent: Nov. 5, 2002

(54) GERANIUM PLANT NAMED 'FISROCORAL'

(75) Inventor: Angelika Utecht, Montabaur (DE)

(73) Assignee: Florfis AG, Binningen (CH)

( * ) Notice: Subject to any disclaimer, the term of this patent is extended or adjusted under 35 U.S.C. 154(b) by 0 days.

(21) Appl. No.: 09/991,950

(22) Filed: Nov. 26, 2001

(65) Prior Publication Data

US 2002/0083506 P1 Jun. 27, 2002

(51) Int. Cl.[7] ..... A01H 5/00

(52) U.S. Cl. ..... Plt./330

(58) Field of Search ..... Plt./330

*Primary Examiner*—Kent L. Bell
(74) *Attorney, Agent, or Firm*—Foley & Lardner

(57) ABSTRACT

A new and distinct cultivar of geranium plant named 'Fisrocoral', as described and illustrated, and particularly characterized by the combined features of deep orange semi-double flowers, large, semi-spherical umbels, medium green foliage with strong zonation, vigorous growth, but well-branched and fairly round plant habit.

1 Drawing Sheet

BOTANICAL CLASSIFICATION

*Pelargonium zonale.*

VARIETY DENOMINATION

'Fisrocoral'.

BACKGROUND OF THE INVENTION

The present invention comprises a new and distinct cultivar of geranium, botanically known as *Pelargonium zonale*, and hereinafter referred to by the cultivar name 'Fisrocoral'.

'Fisrocoral' is a product of a planned breeding program which had the objective of creating new geranium varieties with deep salmon to red flower color in combination with vigorous growth and good outdoors performance.

'Fisrocoral' originated from a hybridization made by the inventor Angelika Utecht in a controlled breeding program in Galdar, Gran Canaria, Spain, in 1996. The female parent was an unpatented hybrid seedling, no. K92-990-1, derived from a cross between the unpatented cultivar 'Fisnida' and the cultivar 'Volcano' (U.S. Plant Pat. No. 5,940). The hybrid seedling was characterized by red, single-type flowers, large inflorescences, and medium green foliage with strong zonation. 'Fisnida' has large inflorescences of orange-red, single-type flowers, medium green foliage with distinct zonation, and fairly vigorous growth, while 'Volcano' has red, semi-double flowers, medium green foliage without zonation, and compact plant habit.

The male parent of 'Fisrocoral' was an unpatented seedling, No. I94-1187-15, originated by self-pollinating the commercial variety 'Isabell', disclosed in (U.S. Plant Pat. No. 7,080). 'Isabell' is characterized by brilliant orange-red, semi-double flowers and medium green foliage with weak zonation. I94-1187-15 is characterized by its orange-red semi-double flowers, medium sized plant habit with relatively large leaves and weak to medium zonation of the foliage.

'Fisrocoral' was selected as one flowering plant within the progeny of the stated cross by Angelika Utecht in 1997, in a controlled environment in Galdar, Gran Canaria, Spain.

The first act of asexual reproduction of 'Fisrocoral' was accomplished when vegetative cuttings were taken from the initial selection in the fall of 1997, in a controlled environment in Galdar, Gran Canaria, Spain, by, or under the supervision of, Angelika Utecht.

Horticultural examination of plants grown from cuttings of the plant initiated in May 1998, in Hillscheid, Federal Republic of Germany, and continuing thereafter, has demonstrated that the combination of characteristics as herein disclosed for 'Fisrocoral' are firmly fixed and are retained through successive generations of asexual reproduction. The new cultivar reproduces true to type.

'Fisrocoral' has not been observed under all possible environmental conditions. The phenotype may vary significantly with variations in environment such as temperature, light intensity and day length. The following observations, measurements, and comparisons describe plants grown in Hillscheid, Germany, and in Langley, British Columbia, Canada, under greenhouse conditions which approximate those generally used in commercial practice.

BRIEF DESCRIPTION OF THE INVENTION

The following traits have been repeatedly observed and are determined to be basic characteristics of 'Fisrocoral' in combination distinguish this geranium as a new and distinct cultivar:

1. Brilliant, deep-orange colored, semi-double flowers;

2. Large, semi-spherically shaped inflorescence, well above the foliage;

3. Medium-green foliage with strong zonation;

4. Vigorous growth, and tall, but uniformly rounded, plant habit; and

5. Medium, mid season spring flowering response.

Of the many commercial cultivars known to the present inventor, the most similar in comparison to 'Fisrocoral' are the patented cultivars 'Fisgrand' (U.S. Plant Pat. No. 8,760), and the related cultivars 'Fismerk' (U.S. Plant Pat No. 12, 444), and 'Fisfire' (U.S. Plant Pat. No. 12,489).

In comparison to 'Fisgrand', 'Fisrocoral' has a somewhat lighter, orange, not orange-red flower color, and larger umbels, stronger zonation on leaves, and even taller, and somewhat more evenly shaped, plant habit.

In comparison to both 'Fismerk' and 'Fisfire', 'Fisrocoral' has a less intense hue of flower color, and distinctly more vigorous growth habit.

BRIEF DESCRIPTION OF THE DRAWING

The accompanying photographic drawing shows typical flower and foliage characteristics of 'Fisrocoral' with colors being as true as possible with an illustration of this type. The drawing shows a flowering pot plant in a 14 cm container.

DETAILED BOTANICAL DESCRIPTION

In the following description color references are made to The Royal Horticultural Society Colour Chart (R.H.S.). The color values were determined indoors from plants developed in a green-house in May 2001, in Hillscheid, Germany. The measurements were taken in Langley, British Columbia, Canada in early July, 2001, 18 weeks after planting of rooted cuttings. The plants were growing in 8 inch containers and had not been pinched.

Inflorescence:
- *Type.*—Umbel.
- *Shape.*—Semi-spherical.
- *Average diameter.*—124 mm.
- *Average depth.*—63 mm.
- *Peduncle length.*—210 mm.
- *Peduncle color.*—Uniform green, RHS 144 A.
- *Pedicel, length.*—35 mm.
- *Pedicel color.*—Green, RHS 144 B, upper part reddish infused, RHS 181 A.
- *Number of flowers per umbel.*—About 30–40.

Corolla:
- *Average diameter.*—49 mm.
- *Form.*—Semi-double.
- *Shape.*—Large, round cup-shaped, occasionally with a narrow gap between upper and lower petals.
- *Number of petals.*—Average 8.6.
- *Number of petaloids.*—0–1, narrow, color like petals.
- *Shape of petals.*—Obovate, base attenuate, upper end is rounded, margin is entire.
- *Size of petals.*—Upper petals length 31 mm, width 22 mm; lower petals length 28 mm, width 24 mm.
- *Color (general tonality from a distance of three meters).*—Deep orange.
- *Color of upper petals.*—Uniform, RHS 40 A.
- *Markings of upper petals.*—Absent, or very weak, fine, dull red veins, RHS 53 D.
- *Color of lower petals.*—RHS 40 A.
- *Markings of lower petals.*—None.
- *Color of lower surface of petals.*—Approximately RHS 43 C.
- *Color of sepals.*—Outer surface light green, RHS 143 C, very weak brown at the base RHS 179 A; inner surface light green, RHS 143 C and RHS 179 B (weak).
- *Number of sepals.*—5.
- *Shape of sepals.*—Linear to lanceolate, acute tip, truncate base, surface with very short pubescence, margin entire.
- *Size of sepals.*—11–12 mm long, 4 mm wide for the largest upper sepal, 3 mm in width for the other sepals.

Bud (just before petals unfold):
- *Shape.*—Elliptical.
- *Color (sepals).*—Green, RHS 144 B.
- *Color (petals).*—RHS 49 C.
- *Length.*—22 mm.
- *Width.*—11–12 mm.

Reproductive organs:
- *Androecium.*—5–7 fertile anthers, filaments white, RHS 155 D, plenty of pollen, orange, RHS 30A.
- *Gynoecium.*—One pistil, style and stigma deep red, RHS 46 B, 5 to 6 lobed stigma.
- *Fertility/seed set.*—Occasionally a few seeds are developed. Fruit: Oblong, about 6 mm in diameter, with rostrum (beak), total length about 42 mm. Seed: Oblong, 4–5 mm long, brown, RHS 177 B.

Spring flowering response period: In Hillscheid, Germany, in 2000 plants had on average 0.8 flowers opened 8 weeks after planting of rooted cuttings.

Outdoor flower production: Continuously flowering, the flower count in 2000 in Hillscheid, Germany, indicated about 2.1 inflorescences per plant in mid May.

Durability: Relatively good stability of flower color, very little fading good resistance to heat and rain.

Lastingness of the individual flower: About 8 days at 18° C., about 18–20 days for the umbel.

Pest/disease resistance/susceptibility: No observations to date.

Fragrance: None.

PLANT

Foliage:
- *Shape.*—Almost round to slightly kidney-shaped, with cordate base, almost no lobes, at the base open.
- *Margin.*—Bicrenated, slightly wavy.
- *Texture.*—Upper surface velvety.
- *Size of leaf.*—102 mm wide, 63 mm long.
- *Color of upper surface.*—Medium green, approximately RHS 137 B to RHS 137 C.
- *Color of zonation.*—Brown, about RHS 166 A, strong and wide.
- *Color of lower surface.*—RHS 137 D.
- *Petioles.*—60–70 mm long, 3.0 mm diameter, light green in color, approximately RHS 143 B.

General appearance and form:
- *Stem color.*—Light green, 144 B to RHS 144 C.
- *Internode length.*—40.0–60.0 mm.
- *Branching pattern.*—Average 8.8 branches.
- *Size of plants.*—Height 34.4 cm, width 51.6 cm, as measured from the top of the soil (base of the main stem) to the surface of the foliage canopy, without inflorescences.

I claim:

1. A new and distinct cultivar of geranium plant named 'Fisrocoral', as described and illustrated herein.

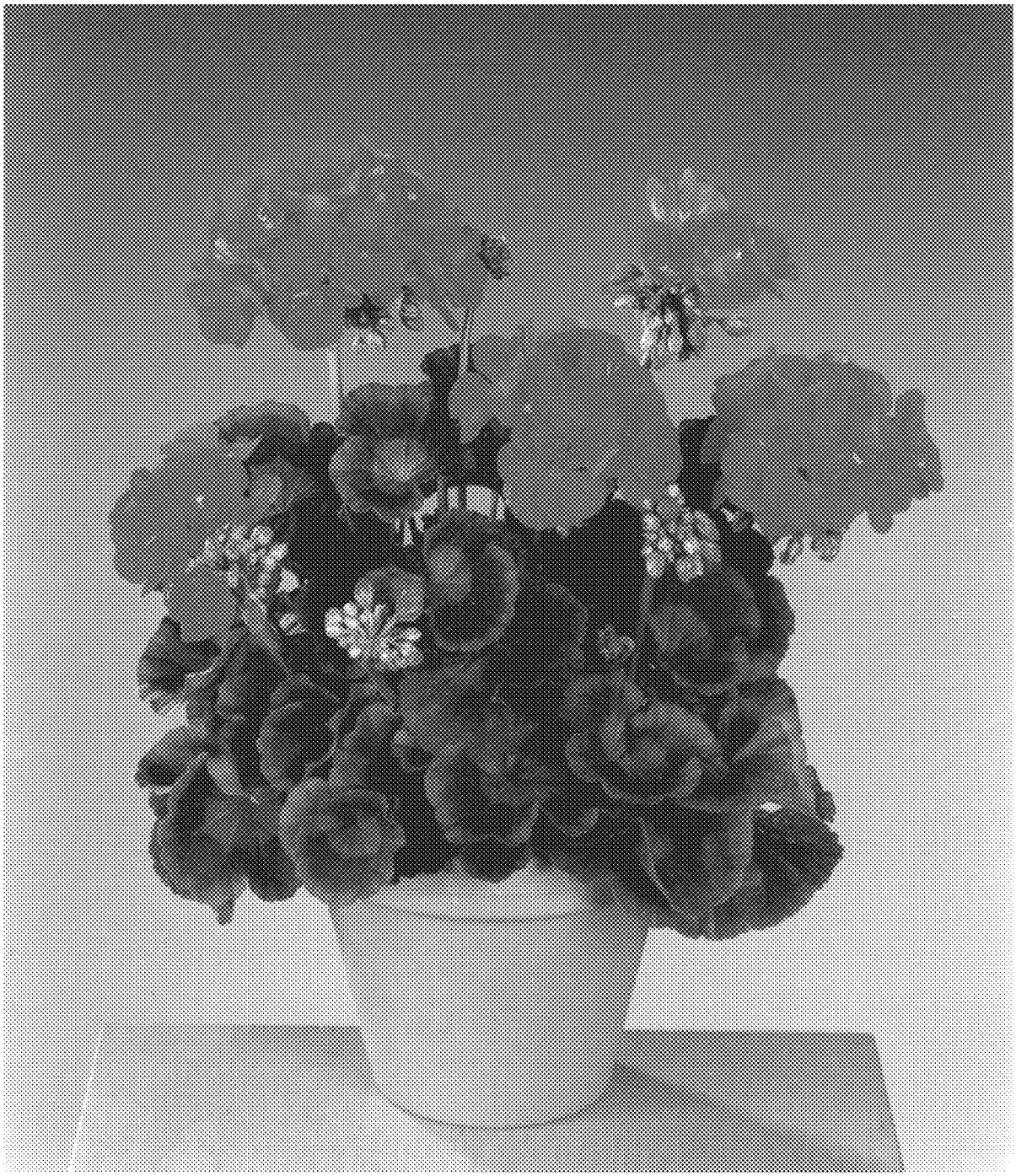

* * * * *